United States Patent [19]

Hosoda et al.

[11] Patent Number: 5,363,106
[45] Date of Patent: Nov. 8, 1994

[54] METHOD FOR EVALUATING INTERNAL QUALITY OF FUSED CAST REFRACTORIES

[75] Inventors: Yutaka Hosoda; Yukihiro Ushimaru; Akinori Samejima, all of Takasago, Japan

[73] Assignee: Asahi Glass Company, Ltd., Tokyo, Japan

[21] Appl. No.: 35,261

[22] Filed: Mar. 22, 1993

[30] Foreign Application Priority Data

Mar. 27, 1992 [JP] Japan .................. 4-101625

[51] Int. Cl.⁵ .............................. G01S 13/02
[52] U.S. Cl. .................................... 342/22
[58] Field of Search ................................ 342/22

[56] References Cited

U.S. PATENT DOCUMENTS 3,562,642  2/1971  Hochschild ............ 342/22 X
4,383,963  5/1983  Ohashi et al. .
4,607,212  8/1986  Jakkula ................ 342/22 X

FOREIGN PATENT DOCUMENTS 2-52272   2/1990  Japan .
2-54191   2/1990  Japan .
2-126176  5/1990  Japan .
4-81679   3/1992  Japan .

Primary Examiner—Gilberto Barrón, Jr.
Attorney, Agent, or Firm—Oblon, Spivak, McClelland, Maier & Neustadt

[57] ABSTRACT

A method for evaluating internal quality of fused cast refractories including the steps of: emitting electromagnetic wave pulses from sending and receiving antennas moving vertically in the vicinity of a side face of a refractory sample through the side face to an inner portion of the sample electromagnetic waves reflected by the sample via by the sending and receiving antennas, thereby obtaining crude reflected wave images; and evaluating an internal structure of the sample based on the picture of reflected wave images. By the present method, an entire inner structure of a fused cast refractory may be evaluated by emitting electromagnetic wave pulses through only by one side face toward a symmetry plane of said fused cast refractory about which the fused cast refractory is symmetrical, and receiving electromagentic waves reflected from an inner surface of the fused cast refractory sample. Therefore, due to the structural symmetry of a fused cast refractory, an internal quality of an entire inner surface of a fused cast refractory may be evaluated on the basis of crude reflected wave images corresponding to a half portion of the fused cast refractory sample.

7 Claims, 4 Drawing Sheets

METHOD FOR EVALUATING INTERNAL QUALITY OF FUSED CAST REFRACTORIES

BACKGROUND OF THE INVENTION

1. Field of the Invention

This invention relates to a method of evaluating the internal quality of fused cast refractories which is performed nondestructively.

2. DISCUSSION OF BACKGROUND

Since fused cast refractories are provided with excellent corrosion resistance against molten glass, fused cast refractories have been employed mainly at portions contacting molten glass of a glass tank furnace. Especially, since fused cast refractories containing a large amount of $ZrO_2$ and having a long service life are used, the service lives of most glass tank furnaces exceed 10 years. However, while a required quality standard of glass products becomes more strict, the operating conditions of the glass tank furnaces likewise become more controlled. Especially, fused cast refractories called "tank blocks" which are employed in side walls of glass tank furnaces require high quality manufacture and operation.

When fused cast refractories are employed in a glass tank furnace, the refractories are preferably lined in accordance with the positions of internal defects thereon so that their service lives are equalized and the service life of the glass tank furnace is not shortened considerably owing to the internal defects of the fused cast refractories. However, when the fused cast refractories of which internal qualities are not sufficiently known, are employed in a glass tank furnace, there are unavoidable cases wherein molten glass flows out from the side walls of the glass tank furnace which was expected to have a sufficient service life, even if dense fused cast refractories, called voidfree (VF) grade are employed. (The VF grade refractory has few defects since a large upper portion of the fused cast refractory having many defects is cut off.)

It is strictly required from users of the glass tank furnaces to precisely evaluate the internal quality of the fused cast refractories so that the above-mentioned troubles are avoided, so that it is possible to dispense with maintenance crews for performing temporarily repairs, and so that a long service life of the glass tank furnace can be ensured.

Recently, the X-ray inspection method or the supersonic inspection method has been commonly employed as a means to investigate the internal qualities of ceramic products. However, in the X-ray inspection method, for the inspection of large-sized ceramic products containing a substance having a low X-ray transmittance, for instance, a substance containing heavy elements such as $ZrO_2$, an X-ray inspection device having a strong X-rays is necessary. Furthermore, in the supersonic inspection method, it is necessary to use a transmission medium such as water or grease to sufficiently transmit the supersonic waves from an oscillator and to receive the reflected supersonic waves from inside of the sample to be inspected, and the measurement is not simple to carry out.

Furthermore, the inspection results are often displayed simply as an image, which is not sufficient as an inspection method for precisely evaluating the internal quality including the position of defects or specifying a state thereof. Especially, when the sample is the fused cast refractory, a precise evaluation is difficult since there are defects inside thereof such as blow holes, flocks of small pores and coarse crystals mixed with pores.

A recent device for searching underground objects has been proposed wherein a laying state of iron codes in reinforced concrete can be detected by electromagnetic waves, as in Japanese Unexamined Patent Publication Nos. 54191/1990, 52272/1990, and 126176/1990. According to this technology, it is possible to detect presence of iron codes laid at approximately 20 cm depth in the reinforced concrete.

In this device for detecting underground objects, sending and receiving antennas moving in parallel with a sample surface emit electromagnetic waves, and receive electromagnetic waves reflected by aboundary (or object) in the sample having different electric properties (dielectric constant), and thus the device provides a distance from the sample surface to the object, based on the time from sending to receiving, and displays the position of the object and the state of the presence thereof in correspondence with the moving position of the sending and receiving antennas, as a computer-processed image.

Furthermore, in Japanese Unexamined Patent Publication No. 81679/1992, a technology is proposed wherein a remaining thickness of refractories of a glass tank furnace is measured by employing such a device, and it is suggested that the technology can be used for shipping inspection of the refractories.

SUMMARY OF THE INVENTION

It is an object of the present invention to solve the drawbacks of the conventional technology in evaluating the internal quality of ceramic products, and especially to provide a practical method for precisely and quantitatively evaluating internal quality of fused cast refractories. This is done by performing an inspection of the fused cast refractories used mainly in a glass tank furnace, utilizing the peculiar characteristics of fused cast refractories.

According to an aspect of the present invention, there is provided a method for evaluating an internal quality of fused cast refractories comprising the steps of:

emitting electromagnetic wave pulses from sending and receiving antennas moving vertically in the vicinity of a side face of a refractory sample to an inner portion of a sample through the side face thereof;

receiving electromagnetic waves reflected by the sample via the sending and receiving antennas thereby obtaining a crude picture of reflected wave images; and evaluating an internal structure of the refractory sample based on the crude picture of reflected wave images.

In this invention, the vertical direction of the fused cast refractory is aligned with respect to a position thereof when it was cast and this condition is kept in the following descriptions. However, in actually performing the inspection of the refractory sample, it is often convenient to perform the inspection in a state wherein the tall fused cast refractory is rotated by 90° and in a sideway state. The method of evaluating an internal quality of fused cast refractories of this invention includes such an embodiment. Such an expression is adopted in order to clarify the positional relationship.

The fused cast refractories are composed of a dense structure having almost no pores except defective portions. This portion of the dense structure is a good transmitter of electromagnetic waves compared with concrete. Therefore, even when defects in the dense structure are comparatively small, the reflected electromagnetic waves can be received, and the method of inspection employing an electromagnetic wave is suitable for the evaluation of the internal quality of the fused cast refractories. When the fused cast refractory is as large as the size which can be employed in the glass tank furnace, the method of evaluating an internal quality of this invention can be employed with almost no problem.

Electromagnetic waves have a property of being reflected at a boundary where the dielectric constant changes. The distance from the surface to the defects at which the electromagnetic waves are reflected, can be represented by the time required for returning the reflected electromagnetic waves. In other words, it is possible to detect the internal defects of the refractory by receiving the reflected waves from the defects in the refractory utilizing the principle of radar.

For this method of evaluating an internal quality of fused cast refractories of this invention, an underground object detector or a detector for objects laid in a concrete mass can be employed. The sending and receiving antennas are composed of a sending antenna and a receiving antenna which are contiguously arranged. The presence of internal defects of the fused cast refractories can be detected by investigating on reflected waves from portions other than the outer surface of the refractory sample. In the method of evaluating internal quality of fused cast refractories of this invention, the purpose can be achieved by analyzing the reflected waves at positions wherein almost no reflected wave images from the surface are superposed.

In this method, the inspection can be made in a noncontacting way owing to the property of the electromagnetic wave without using a transmitting medium such as water or grease as in the method utilizing supersonic waves. It is not necessary to pay attention to the surface condition of the sample. The reproducibility of the inspection result is good. Furthermore, when the inspection device is provided with an image processing function wherein a microcomputer is integrated by adopting the recent progress of electronics, the device can be provided with a good operational performance and can be employed for inspecting the internal quality of the fused cast refractories at the production site.

The fused cast refractories are produced by casting and solidifying molten refractory material in sand molds or in graphite molds. In many cases, the fused cast refractories are provided with shapes having symmetry planes or a pair of parallel opposing planes in the vertical direction. That is, the molten material is cast into a mold having a pair of parallel internal faces. At this occasion, the sensible heat of the molten substance and the latent heat generated in its solidification flow from inside of the refractory to walls of the mold surrounding the refractory. Therefore, the solidification starts from the surface of the refractory and proceeds into the inner portion thereof.

Furthermore, since the volume of the molten substance is reduced in the solidification, the free surface of the molten substance gradually moves downward, and causes blow holes in the upper central portion of the refractory. Therefore, a portion called a melt feeding port is provided at the upper portion of the mold and the molten substance is additionally poured into the portion and the solidified melt feeding port having blow holes is cut off after its casting.

When the solidification of the refractory material proceeds, there arises a difference of chemical composition between a part which solidifies at first and a part which solidifies later. The crystals of the rapidly solidified part are small and the crystals of the gradually solidified part are generally large. Elongated prismatic crystals are formed in the direction of crystal growth. Therefore, the structure in the fused cast refractory normally changes in accordance with the position thereof.

When the solidification proceeds further, even if the thermal conduction is controlled such that the solidification proceeds from the bottom, the molten substance often can not move downwardly. Then the solidification proceeds in an enclosed space. Void gaps (called blow holes) corresponding to the shrink volume of the solidified molten substance are formed in the refractory.

With respect to the structure of the fused cast refractory, when the shape of the refractory is provided with a vertical symmetry plane, the fused cast refractory will be provided with a structure which is almost symmetrical with respect to the symmetry plane, since the temperature distribution inside the fused cast refractory during the solidification is symmetrical with respect to the symmetry plane.

In this case, electromagnetic wave pulses are emitted towards the symmetry plane from one of the side faces of the fused cast refractory which is approximately parallel to the symmetry plane. Since the structure has this symmetry, it is not necessary to analyze all of the images obtained by the reflected waves. It is possible to evaluate the entire internal quality of the fused cast refractory from a part of the reflected wave images. In this method of evaluating an internal quality of fused cast refractories of this invention, since the symmetry of the internal structure of the refractory with respect to the symmetry plane is almost established, the evaluation of the internal quality of the total of the fused cast refractories can be facilitated.

The sending and receiving antennas are disposed in the vicinity of the refractory sample so that the noises of the reflected waves from the surrounding object can be neglected. The sample is scanned by the electromagnetic wave pulses emitted from the sending and receiving antennas moving vertically. The scanning is preferably performed by moving the sending and receiving antennas parallel to one another along a side face of the sample. The emitted electromagnetic wave pulses normally have a considerable scope angle (for instance 90°), at which they are reflected by the incident side face of the sample, internal defects, the back side face opposite to the incident side face, and the other side faces and boundary faces to be received by the sending and receiving antennas. The reflected waves include noise waves being reflected by the incident and back side faces at plural times, which are called multiply reflected waves.

It is possible to detect the position where the electromagnetic wave is reflected with respect to the vertical position of the fused cast refractory by receiving the reflected electromagnetic waves by moving the sending and receiving antennas. It is possible to provide an image picture of reflected waves of the refractory including the reflected wave images from the surface which correspond to the vertical section of the fused cast refractory by scanning the same with the electromagnetic wave pulses. It is possible to at once display the image picture of reflected waves on a display of the inspection device integrated with a microcomputer.

In a preferred embodiment of the method of evaluating internal quality of fused cast refractories of this invention, a processed picture of reflected waves is provided by removing noise images of reflected waves caused by the surface or the surfaces of the sample from the crude picture of reflected wave images, or by removing the reflected noise waves caused by the surface or surfaces of the sample from the received reflected waves of the sample. Thereby, the evaluation of internal quality of the sample utilizing the processed picture of reflected wave images is facilitated.

A simple method of removing the images caused by the surface reflected waves is that a reflected wave image picture of fused cast refractories having no defects (only surface reflected wave images are present) is separately provided, this surface reflected wave image picture is subtracted from the reflected wave image picture of the sample, and a processed picture of reflected wave images caused only by the internal defects, is provided. In this subtraction, it is not always necessary to remove the surface multiply reflected images which are present in the picture in the vicinity of the single reflected wave image from the back surface of the sample.

In specifically providing a reflected wave image of the refractory sample having no surface reflected wave image, the image pattern of the surface reflected wave is memorized in memories of a microcomputer of the inspection device, and the subtraction of the surface reflected waves or the surface reflected wave images are automatically performed. In this way, the processed reflected wave image picture can be provided from which is removed of the surface reflected wave caused by the surface of the sample. Furthermore, when the sectional shape of the refractory sample does not change in the vertical position, it is possible to obtain the processed reflected wave image picture with the surface reflected wave images removed simply by subtracting the surface reflected wave images provided by the portion having no internal defects. When the emitted electromagnetic wave pulses are accompanied by a noise (secondary wave), the interpretation of the reflecting wave image is further facilitated by performing the removal of the reflected noise waves (subtraction) simultaneously with the removal of the multiply reflected waves.

In another preferred embodiment of a method of evaluating internal quality of fused cast refractories of this invention, the evaluation of the refractory sample is performed based on the reflected wave images with respect to a half portion of the reflected wave image picture between the incident side face and the center plane (the vertical symmetry plane) at half of the distance from the incident side face to the back side face.

By adopting the method of emitting the electromagnetic wave pulses toward the vertical symmetry plane of the fused cast refractory, when an analysis is performed on half of the obtained reflected wave image picture, the whole evaluation of the fused cast refractory can be performed.

Furthermore, with respect to obtained images, there are light and deep portions. An investigation is performed on reflected wave images of the image picture with respect to half of the distance from the incident side face to the back side face. It was confirmed that the deep portion of the image corresponds to a large defect such as a blow hole or an aggregation of coarse crystals, whereas the light portion of image corresponds to a defects such as small pores or coarse crystals, by cutting the refractory sample and comparing the cut sample with the images obtained by the inspection test. Furthermore, it was found that the integrated area of the deep images and the integrated area of light images designate the sizes or the degrees of the respective defects.

In another preferred embodiment of a method of evaluating internal quality of fused cast refractories of this invention, the evaluation of the refractory sample is performed by emitting the electromagnetic wave pulses towards the vertical symmetry plane of the sample from a direction approximately orthogonal to the vertical symmetry plane of the sample. In obtaining the reflected wave images, it is possible to minimize reflected wave images which are hard to interpret, by adopting such a positional relationship with the symmetry plane of the sample, and therefore, it is possible to perform the evaluation of the internal quality easily and with good reliability.

In another preferred embodiment of a method for evaluating internal quality of fused cast refractories of this invention, the refractory sample is partitioned to 1, 2, ..., n parts by (n−1) assumed horizontal planes, the reflected wave image picture is divided into 1, 2, ..., n portions respectively corresponding to the parts partitioned in the sample, and the respective parts of the sample are evaluated based on the respective portions of the divided picture of reflected wave images.

For example, the sample is partitioned into 4 parts by 3 assumed horizontal planes and the obtained reflected wave image picture is divided into 4 portions corresponding to the respective parts. When the fused cast refractory is partitioned into 1, 2, 3 and 4 parts from the top portion (1 is on the side of a casting port wherein the melt feeding port is cut off), the reflected wave image picture is divided into corresponding 1, 2, 3 and 4 portions, and the evaluation with respect to each part can be performed.

The internal quality evaluation with respect to each part may, for instance, be performed in the following way. With respect to a half portion of the reflected wave image picture up to a half depth from the incident side face, each summed area of deep images and each summed area of light images in 1, 2, 3 and 4 portions are measured with respect to each part, and the qualities of the respective parts are shown by A, B, C and D or by evaluation values ($T_i$) based on a standard shown in Table 1.

TABLE 1

| Summed area of light images (H) | Summed area of deep images (G) | Evaluation value | Evaluation of structure |
| --- | --- | --- | --- |
| 0 mm$^2$ | 0 mm$^2$ | 0 point | A |
| <50 mm$^2$ | 0 mm$^2$ | 5 points | B |
| 50~100 mm$^2$ | ~25 mm$^2$ | 50 points | C |
| >100 mm$^2$ | >25 mm$^2$ | 200 points | D |

By performing the evaluation of the inner quality with respect to the respective parts, the qualities of the respective parts can be shown for the respective fused cast refractory parts. When the fused cast refractories are used in a glass tank furnace, it is possible to prolong the service life of the glass tank furnace by lining with the fused cast refractories in consideration of the inner qualities of the respective parts. Furthermore, the present method is useful as a inspection means for determining preferable casting conditions by changing the casting conditions of the fused cast refractories, and it is not necessary to inspect the inside thereof by cutting the cast samples.

In another preferred embodiment of a method of evaluating internal quality of fused cast refractories of this invention, in addition to the evaluation of each part of the refractory sample, a total evaluation is performed wherein the total evaluation of the sample is performed by weighting the evaluated values of parts and summing the weighted values. In this way, the total evaluation of the inner quality corresponding to the practical performance of the fused cast refractories can be made.

Next, an explanation will be given of an example of the quantitative total evaluation method of the refractory sample. This evaluation method is performed by previously determining a calculation formula considering the weighting rate, for instance, with respect to the importance of each part.

For instance, when the sample is partitioned into 4 parts of 1, 2, 3 and 4, the evaluated values of the respective parts are $T_1$, $T_2$, $T_3$, $T_4$ (it is assumed that part 4 is disposed at an inner side of the glass furnace and is used in contact with the molten glass which most necessitates the corrosion resistance the most). For example, the weighting rate considering the importance of each part is 1, 2, 3 or 4, respectively. The total evaluation of the refractory sample is performed by calculating with the formula of $(T_1 \times 1 + T_2 \times 2 + T_3 \times 3 + T_4 \times 4)/4$. In this method for evaluating an internal quality of smaller the provided numerical value is, the better is the quality of the fused cast refractory.

DETAILED DESCRIPTION OF THE PREFERRED EMBODIMENTS

Figure 1:
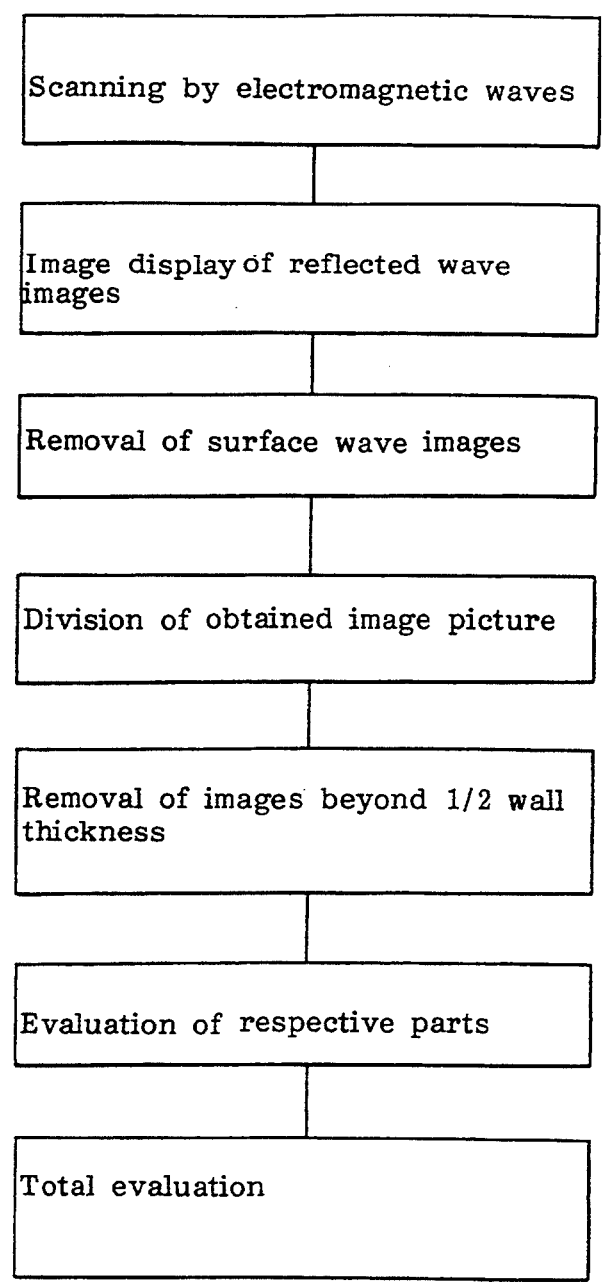
FIG. 1 is a flowchart for explaining a typical example of a method for evaluating an internal quality of fused cast refractories of this invention.

A specific explanation will be given of the present invention with respect to each of the aove mentioned embodiments. However, this invention is not restricted by these examples. FIG. 1, is a flowchart showing an example of a method of evaluating internal quality of fused cast refractories according to the present invention, and the following embodiments were performed in accordance with the procedure of the flowchart.

The tested sample was a fused cast refractory for glass tank furnaces called ZB1691 made by Asahi Glass Company Ltd., which contains at least 35 wt % of $ZrO_2$. The dimension of the sample was 250 mm×450 mm×1200 mm and the weight of the sample was approximately 513 kg. The refractory sample was put in a laid down and rotated by 90° so that the face of the top side (the top face of the refractory sample at which the melt feeding port was cut off) of the fused cast refractories was on the righthand side.

As an inspection device utilizing electromagnetic waves, an inner objects detector for concrete was employed. The inspection device was integrated with a microcomputer having an image processing function and provided with an image display and a printer for drawing the displayed image was attached thereto.

The employed electromagnetic waves are electromagnetic wave pulses having a width of 1 nanosecond (an electromagnetic wave pulse discharged from an oscillator was a single wave of a triangular shape, and an electromagnetic wave emitted from an antenna was an aggregation of a plurality of triangular electromagnetic waves). The sending and receiving antennas are placed facing the face of dimensions 450 mm×1200 mm which is the rotated top face. In the internal inspection of the refractory, the scanning was performed by emitting the electromagnetic wave pulses while moving the sending and receiving antennas along the face in the horizontal direction (in the vertical direction with respect to the positional relationship taken in its casting).

Figure 2:
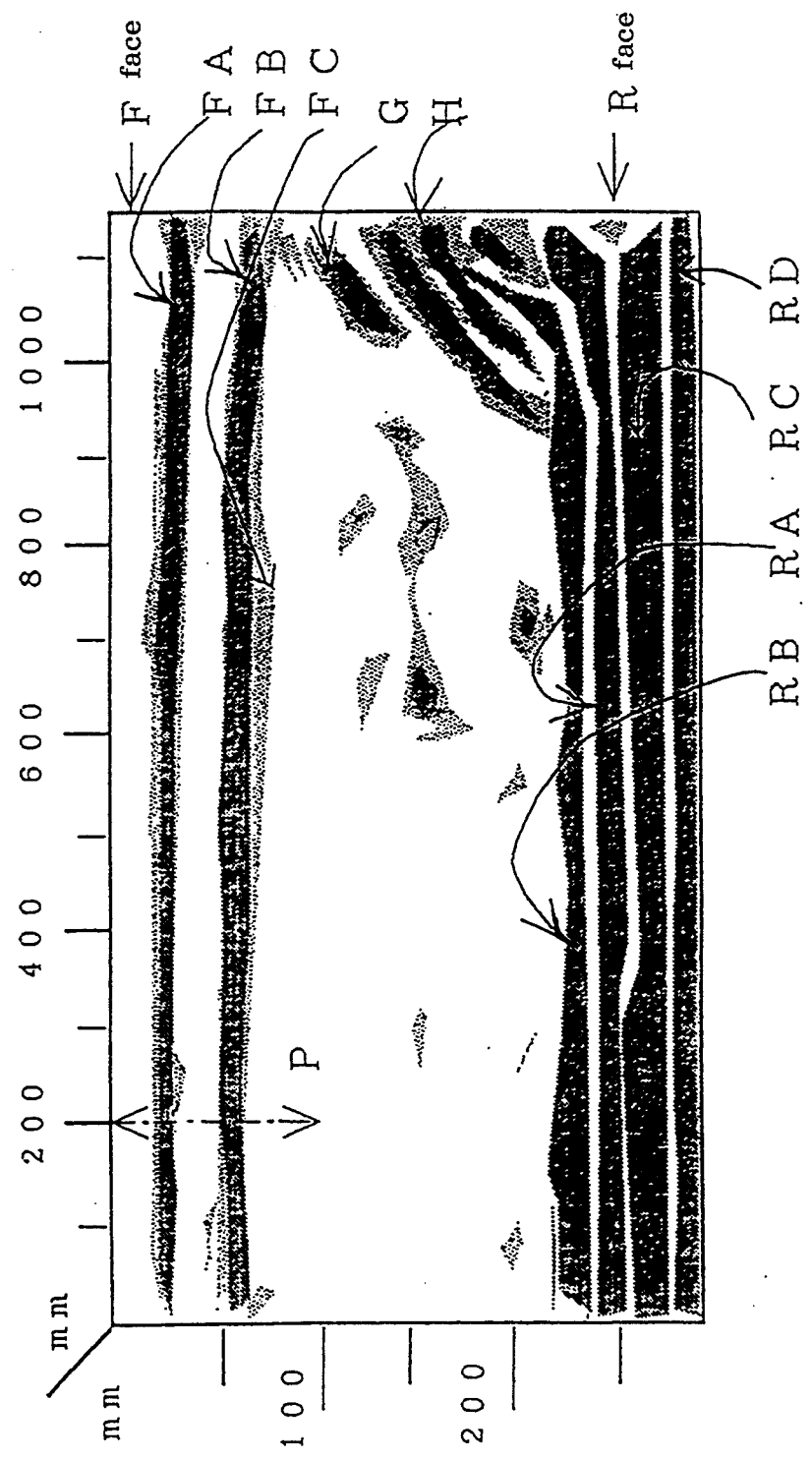
FIG. 2 is an example of a reflected wave image picture before removing surface reflected wave images provided by the method for evaluating internal quality of this invention.

The electromagnetic waves reflected by scanning the refractory sample by the electromagnetic wave pulses were received by the sending and receiving antennas. FIG. 2 shows an example of reflected wave images displayed on the display of the inspection device. In FIG. 2, F-face designates a side face upon to which the electric wave pulses are emitted, and R-face, another side face reverse to the side face upon to which the electromagnetic waves are emitted. The righthand side of the diagram corresponds to the face at which the melt feeding port in casting was cut off (the top side in the casting). In the reflected wave image picture, the surface reflected wave images FA, FB, FC, RA, RB, RC and RD are displayed bandwisely.

An explanation will be given of a method of removing the surface reflected images from the crude reflected wave image picture. The reflected wave image, for instance, in the vicinity of a one-dotted chain line P wherein the internal defects are not substantially present, was adopted as the subtracting surface reflected wave images. The surface reflected wave image FA and its multiply reflected wave images FB and FC were generated owing to the F-face when the sending and receiving antennas are directed in the direction of P, and the surface reflected wave image RA caused by the R-face and its multiply reflecting wave images RB, RC and RD (RC and RD images are located below the position corresponding to the R-face in the reflected wave image picture). When the reflected wave image picture of the total sample was to be investigated further, these reflected wave images were stored in the memory of the microcomputer as the reference signals, which were subtracted from the crude reflected wave image picture thereby deleting (processing) the surface reflected images.

Figure 3:
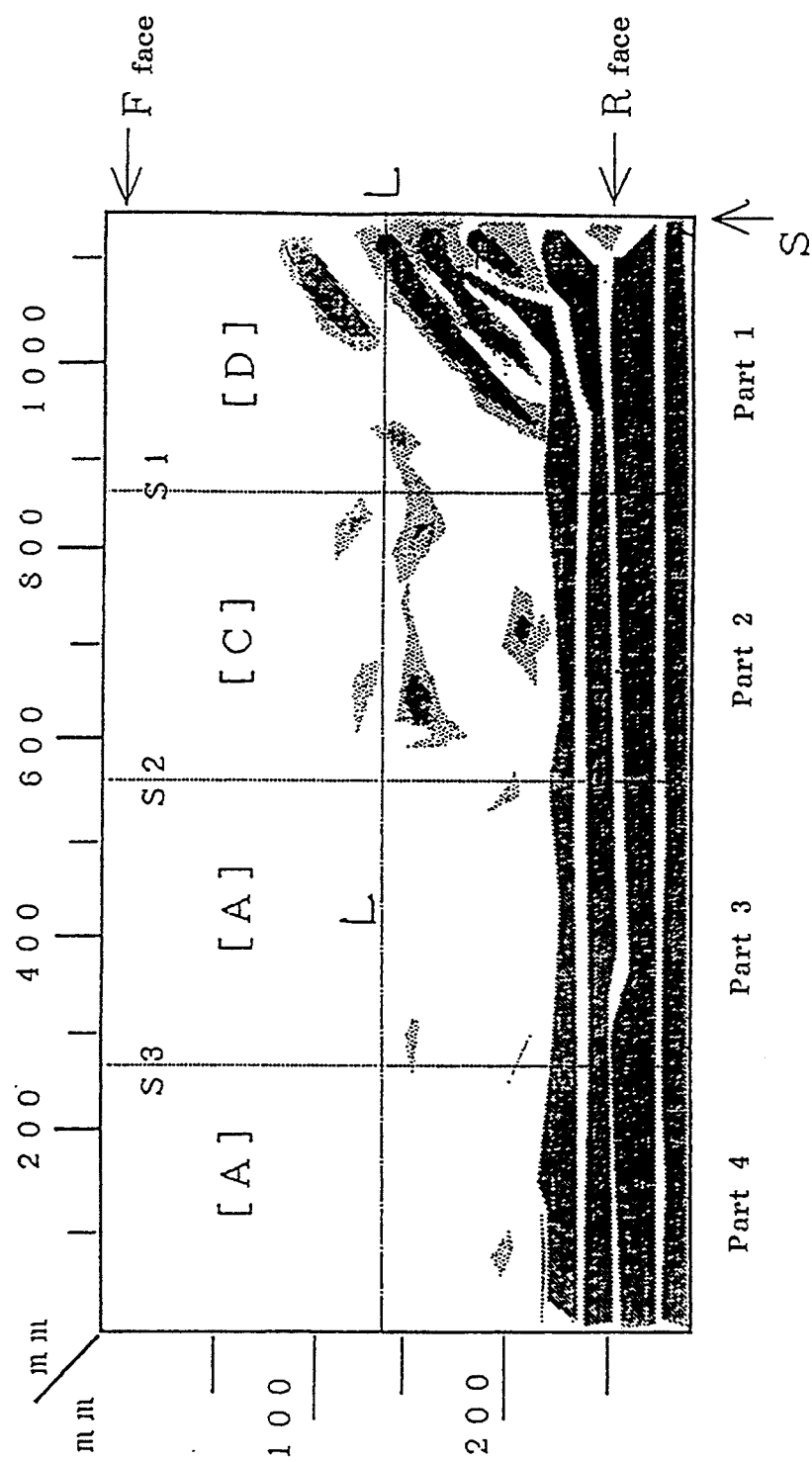
FIG. 3 is the reflected wave image picture after portions of the surface reflected wave images are removed from the picture of FIG. 2.

FIG. 3 shows the processed reflected wave image picture wherein the noises of the surface reflected images FA, FB and FC were removed. The reason why the surface reflected images RA, RB, RC and RD remain in FIG. 3 is that since the fused cast refractories were provided with the symmetry plane, the inspection of the total sample can sufficiently be performed by analyzing the reflected wave images of the half portion between the incident surface of the electromagnetic waves and the symmetry plane and, therefore, these surface reflected wave images were not removed.

In FIG. 2, deep images G designate the reflected wave images caused by blow holes or by an aggregation of coarse crystals, and light images H, weak reflected wave images caused by coarse crystals or fine pores. These were confirmed by cutting a number of inspected fused cast refractories and observing their sections and comparing the images. As shown in FIG. 3, the refractory sample is partitioned into, for instance, 4 parts in the height direction. That is, the height of the fused cast refractory, 1200 mm, is divided into 4 parts with a pitch of 300 mm, and the parts 1, 2, 3 and 4 are evaluated to perform the total evaluation of the fused cast refractory.

As shown in FIG. 3, the height of refractory sample from the bottom to the cut surface S wherein the solidified casting port (melt feeding port) of the fused cast refractories is horizontally cut off, is partitioned by assumed horizontal planes S1, S2 and S3, and the reflected wave image picture is divided into the respective portions 1, 2, 3 and 4 corresponding to the respective parts as shown in FIG. 3. The partition number n can be increased in accordance with the necessity and the parts evaluation may be performed finely.

In case of the fused cast refractory, it was possible to grasp the total quality of the refractory by the inspection up to the depth of a half thickness as mentioned before. This was performed in the following way. The explanation will be given in reference to FIG. 3. A straight line L is drawn at the position (125 mm apart from the F-face) of a half of the thickness (250 mm) of the refractory in the reflected wave image picture. The evaluation was made on the images up to the half depth on the side adjacent to the incident face or above the straight line L (noise images up to the half thickness are removed).

In case of the fused cast refractory, almost no reflected wave image from R-face appears on the side of the F-face of the straight line L (or, it is easy to control the reflected wave image picture such that the reflected wave image of R-face does not appear on the F-face side of the straight line L). Therefore, it is sufficiently possible to perform the evaluation even when the surface reflected wave image of the R-face is not removed.

For instance, the evaluation on each part was performed as follows. The reflected wave images on the side of the F-face of the straight line L are classified into deep images and light images, with respect to every part partitioned by the straight lines S1, S2 and S3 and the total areas for the respective classified images were provided. Both image areas were compared with the standard image evaluation table shown in Table 1 and the evaluation of structure A, B, C and D or the evaluated point value was determined for every part. Table 2 shows an example of the evaluated result. Furthermore, when a more detailed evaluation is necessary, another inner quality evaluation wherein electromagnetic waves are emitted upon a contiguous side face of the fused cast refractory having a shape of a rectangular parallelepiped, or wherein the electromagnetic waves are emitted upon an opposite side face, may additionally be performed.

TABLE 2

| Part | Evaluation of structure | Evaluation value |
| --- | --- | --- |
| 1 | [D] | 200 points |
| 2 | [C] | 50 points |
| 3 | [A] | 0 point |
| 4 | [A] | 0 point |

Furthermore, the total evaluation was, for instance, performed as follows. In this example, a large weighting rate was attached to the part 4 (assuming that the part 4 was disposed at the inner side of the glass tank furnace and the evaluation value of part 4 in Table 2 was multiplied by 4 and the products were summed.

$$(200 \times 1 + 50 \times 2 + 0 \times 3 + 0 \times 4)/4 = 75$$

Figure 4:
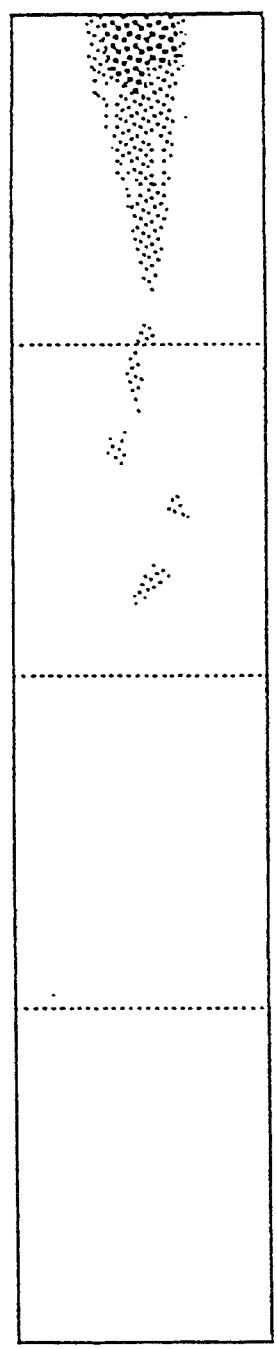
FIG. 4 is an example of vertical section of a fused cast refractory to which the method for evaluating internal quality of this invention is applied.

FIG. 4 is a schematic illustration showing an example of a section of a voidfree (wherein the solidified melt feeding port having many blow holes was cut off) grade fused cast refractory which was cut in the vertical direction after the internal quality evaluation of the present method was performed. The dark portion in FIG. 4 shows a blow hole or a pore. As a result of evaluating the internal quality of a number of fused cast refractories by the present method and comparing the test result with the internal defects found by actually cutting the refractories, it was confirmed that the internal quality evaluation method of this invention is a method capable of precisely evaluating the internal quality of the fused cast refractory.

The present internal quality evaluation method for fused cast refractories, is applicable to evaluation an internal quality of press-formed bricks or cast bricks. In this case, side faces approximately orthogonal to the direction of a thinner thickness (normally there are two side faces on the front side and on the back side), are selected so that transmitted electromagnetic waves are easy to reach defects and reflected waves are easy to receive. The sending and receiving antennas are disposed in the vicinity of one of the side faces. The electromagnetic wave pulses are emitted toward the inner portion of the brick while moving the sending and receiving antennas along the side face of the brick and the reflected waves are received.

When the sample is a press-formed brick or a cast brick, a side face adjacent to a portion having a large locating possibility of defects among both side faces the brick sample in a direction of a thinner thickness is selected. The electromagnetic wave pulses are emitted from the side face of the sample towards the inside thereof, while moving the sending and receiving antennas in the vicinity of the side face. The reflected wave image picture of the sample is provided by receiving reflected electromagnetic waves from the brick sample by the sending and receiving antennas. The inner structure of the sample is evaluated based on the reflected wave images.

This method utilizes the fact that the defects are apt to be caused adjacent to one side face in the formed brick (for instance, in a case of the press-formed brick "lamination" is apt to be caused in the vicinity of the side face contacting a piston mold). When the internal defects are present only near to the side face wherein the sending and receiving antennas are disposed, it is possible to easily evaluate the internal quality of the brick by following the same steps as in the case of the fused cast refractory.

According to the present method of evaluating the internal quality of fused cast refractories, the evaluation can be performed nondestructively with good operational performance on the production site without utilizing large-scaled equipment. Even with small defects present inside thereof, the position and the degree can precisely and easily be determined by utilizing the symmetrical structure of the fused cast refractory with respect to the vertical symmetry plane formed when it is cast. Therefore, the present method is suitable for the quality control and evaluation of fused cast refractories.

A significant effect can be achieved in expanding the service life and ensuring the reliability of a glass tank furnace by lining the glass tank furnace with fused cast refractories in consideration of the evaluated data including the positions and sizes of defects inside the fused cast refractories.

What is claimed is:

1. A method for evaluating an internal quality of a fused cast refractory comprising the steps of:

emitted electromagentic wave pulses from antenna means through exactly one side of face of a fused cast refractory sample toward a symmetry plane thereof about which a structure of said fused cast refractory is symmetrical, said antenna means moving along a side face of said fused cast refractory sample;

receiving electromagnetic waves reflected from an inner portion of said fused cast refractory sample via said antenna means, thereby obtaining crude reflected wave images of said inner portion of said fused cast refractory sample; and evaluating an internal structure of said fused cast refractory sample on the basis of said crude reflected wave images, wherein said side face of said fused cast refractory sample is aligned approximately parallel to said symmetry plane.

2. The method for evaluating an internal quality of a fused cast refractory accordingly to claim 1, wherein a processed picture of said crude reflected wave images is provided by removing noise images from reflected electromagentic waves caused by a surface of said fused cast refractory sample.

3. The method for evaluating an internal quality of a fused cast refractory according to claim 2, wherein a processed picture of said crude reflected wave images is provided by removing refelected electromagnetic noise waves caused by a surface of said fused cast refractory sample from electromagnetic waves refelcted from said inner portion of said fused cast refractory sample.

4. The method for evaluating an internal quality of a fused cast refractory according to claim 1, wherein an internal quality of an entire internal structure of said fused cast refractory sample is evaluated on the basis of said crude reflected were images corresponding to a half portion of said internal surface of said fused cast refractory sample positioned between said side face through which said electromagnetic wave pulses are emitted and said symmetry plane.

5. The method for evaluating an internal quality of a fused cast refractory according to claim 1, wherein said internal structure of said fused cast refractory sample is evaluated by emitted electromagentic wave pulses toward said symmetry plane of said fused cast refractory sample so that said electromagnetic wave pulses impinge orthogonally thereupon.

6. The method for evaluating an internal quality of a fused cast refractory according to claim 1, wherein said fused cast refractory sample is partitioned into n imaginary parts by $(n-1)$ imaginary planes aligned orthogonal to said symmetry plane, and said crude reflected wave image are correspondingly divided into n portions, and wherein internal structures of each of said n imaginary parts of said fused cast refractory sample are evaluated on the basis of respective portions of said crude reflected wave images.

7. The method for evaluating an internal quality of a fused cast refractory according to claim 6, wherein, in addition to internal quality evaluations of each of the n imaginary parts of said fused cast refractory sample, a total internal quality evaluation of an entire inner portion of said fused cast refractory sample is performed by weighting an evaluated value for each said n imaginary parts thereof and summing weighted evaluated values corresponding to each of said n imaginary parts.

* * * * *